(12) United States Patent
Vaporciyan

(10) Patent No.: US 8,309,750 B2
(45) Date of Patent: Nov. 13, 2012

(54) PROCESS FOR THE PREPARATION OF A DIARYL CARBONATE

(75) Inventor: Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 783 days.

(21) Appl. No.: 12/194,422

(22) Filed: Aug. 19, 2008

(65) Prior Publication Data

US 2009/0131706 A1    May 21, 2009

(30) Foreign Application Priority Data

Aug. 20, 2007    (EP) .................................... 07114618

(51) Int. Cl.
*C07C 69/96* (2006.01)

(52) U.S. Cl. ........................................ 558/274; 558/270

(58) Field of Classification Search ................. 558/270, 558/274
See application file for complete search history.

(56) References Cited

U.S. PATENT DOCUMENTS

| | | | |
|---|---|---|---|
| 3,642,858 A | 2/1972 | Fevel et al. | |
| 3,803,201 A | 4/1974 | Gilpin et al. | |
| 3,959,354 A | 5/1976 | Onoda et al. | |
| 4,045,464 A | 8/1977 | Romano | |
| 4,182,726 A | 1/1980 | Illuminati et al. | |
| 4,352,940 A | 10/1982 | Adelman et al. | |
| 4,515,983 A | 5/1985 | Goel et al. | |
| 4,533,504 A | 8/1985 | Bolon et al. | |
| 5,113,015 A | 5/1992 | Palmer et al. | |
| 5,210,268 A | 5/1993 | Fukuoka et al. | |
| 5,334,742 A | 8/1994 | Schon et al. | |
| 5,344,954 A | 9/1994 | Schon et al. | |
| 5,349,102 A | 9/1994 | Tuinstra et al. | |
| 5,426,207 A | 6/1995 | Harrison et al. | |
| 5,426,245 A | 6/1995 | Hamada et al. | |
| 5,543,546 A | 8/1996 | Tsuneki et al. | |
| 5,663,480 A | 9/1997 | Tsuneki et al. | |
| 5,705,673 A | 1/1998 | Rivetti et al. | |
| 5,747,609 A | 5/1998 | Komiya et al. | 526/68 |
| 5,874,605 A | 2/1999 | Yoshida et al. | |
| 6,342,620 B1 | 1/2002 | Mori | |
| 6,407,279 B1 | 6/2002 | Buchanan et al. | |
| 6,528,679 B1 | 3/2003 | Mori et al. | |
| 6,573,396 B2 | 6/2003 | Buchanan et al. | |
| 7,084,291 B2 * | 8/2006 | Soloveichik et al. | 558/274 |
| 7,312,352 B2 * | 12/2007 | Buckley et al. | 558/274 |
| 7,777,067 B2 * | 8/2010 | Fukuoka et al. | 558/274 |
| 2002/0183549 A1 | 12/2002 | Lee | |

FOREIGN PATENT DOCUMENTS

| | | |
|---|---|---|
| EP | 684221 | 11/1995 |
| EP | 760359 | 3/1997 |
| JP | 5004935 | 1/1993 |
| JP | 5310623 | 11/1993 |
| JP | 2000281622 | 11/1993 |
| JP | 6256241 | 9/1994 |
| JP | 6256242 | 9/1994 |
| JP | 5310622 | 10/2000 |
| JP | 2000281620 | 10/2000 |
| JP | 2000281621 | 10/2000 |
| JP | 2000281623 | 10/2000 |
| JP | 2001097922 | 4/2001 |
| JP | 20001097920 | 4/2001 |
| JP | 20001097921 | 4/2001 |
| JP | 2001163830 | 6/2001 |
| WO | WO9517371 | 6/1995 |
| WO | WO9747586 | 12/1997 |

* cited by examiner

*Primary Examiner* — Golam M M Shameem

(57) ABSTRACT

The invention relates to a process for the preparation of a diaryl carbonate, which comprises: (i) contacting an aromatic non-hydroxy compound with a carboxylic acid of formula $HOC(=O)R^1$ (I), wherein $R^1$ is a hydrocarbyl group, and with an oxygen containing gas in the presence of a catalyst, resulting in water and an aromatic carboxylic acid ester of formula $R^2OC(=O)R^1$ (II), wherein $R^2$ is an aryl group originating from the aromatic non-hydroxy compound; and (ii) contacting the aromatic carboxylic acid ester of formula (II) from step (i) with a dialkyl carbonate of formula $R^3OC(=O)OR^4$ (III), wherein $R^3$ and $R^4$ are the same or different and are alkyl groups, in the presence of a catalyst, resulting in a diaryl carbonate of formula $R^2OC(=O)OR^2$ (IV) and an alkyl carboxylic acid ester of formula $R^5OC(=O)R^1$ (V), wherein $R^5$ is $R^3$ or $R^4$.

16 Claims, No Drawings

PROCESS FOR THE PREPARATION OF A DIARYL CARBONATE

CROSS REFERENCE TO RELATED APPLICATION

This application claims priority to European Patent Application number EP 07114618.7 filed Aug. 20, 2007, the entire disclosure of which is herein incorporated by reference.

FIELD OF THE INVENTION

The present invention relates to a process for the preparation of a diaryl carbonate.

BACKGROUND OF THE INVENTION

Diaryl carbonates are important starting materials for the production of aromatic polycarbonates, hereinafter sometimes referred to simply as polycarbonate. Polycarbonate is a widely used raw material in many different manufacturing sectors. Due to the high hardness as well as good transparency of the material, it can be applied in applications as diverse as automotive windows and optical lenses. The demand for polycarbonate is believed to increase largely within the next years, which will require the production of polycarbonate to be improved in terms of efficiency and environmental impact.

Polycarbonates can be manufactured by polymerisation of a diaryl carbonate with an aromatic dihydroxy compound. Said aromatic dihydroxy compound may be bisphenolacetone (BPA or bisphenol A), i.e. 2,2-bis(4-hydroxyphenyl) propane. The production of polycarbonate by the polymerisation of diaryl carbonate with an aromatic dihydroxy compound is known from U.S. Pat. No. 5,747,609. This document also describes the production of diaryl carbonate from dialkyl carbonate with an aromatic alcohol. In this reaction a transesterification of dialkyl carbonate takes place whereby overall the diaryl carbonate is produced and as by-product alkanol is obtained. The dialkyl carbonate can be produced from an alkylene carbonate and an alkanol. This reaction yields as useful products not only the dialkyl carbonate that can be used for the preparation of diaryl carbonate, but also a useful alkanediol. For this reaction one may use the alkanol that has been liberated in the transesterification of dialkyl carbonate and aromatic alcohol.

In general, the above-mentioned direct reaction of a dialkyl carbonate with an aromatic alcohol producing a diaryl carbonate is not favored thermodynamically. For example, the reaction of dimethyl carbonate and phenol has an equilibrium constant of $Keq=10^{-7}$. This implies that large excesses of reagents are necessary to produce diaryl carbonate. As a consequence, large reactors are necessary which increases overall costs and therefore diminishes efficiency.

Another known process for producing a diaryl carbonate from an aromatic alcohol is one wherein the aromatic alcohol, such as phenol, is reacted with phosgene ($COCl_2$) instead of a dialkyl carbonate. However, this process has the inherent drawbacks of employing the harmful phosgene and creating chloride containing waste streams. Therefore, the use of phosgene evidently has a negative environmental impact.

Solutions to the disfavored reaction equilibria in the reaction of dialkyl carbonate with aromatic alcohol have been suggested. These solutions still involved the use of aromatic alcohol but no longer comprised a direct reaction of said alcohol with the dialkyl carbonate. The aromatic alcohol was converted into an intermediate that had a more favorable reaction equilibrium with dialkyl carbonate than the aromatic alcohol as such.

For example, in U.S. Pat. No. 5,543,546, it is proposed that in a first step phenol (PhOH) is converted into phenyl propionate and methanol (MeOH), by reacting it with methyl propionate. In a second step, the intermediate phenyl propionate is reacted with dimethyl carbonate (DMC) into methyl propionate and the desired diphenyl carbonate (DPC). The methyl propionate formed in the second step is recycled to the first step. The reactions in said two steps and the net reaction of the integrated process wherein methyl propionate is recycled are shown below:

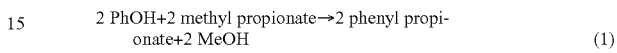

2 PhOH+2 methyl propionate→2 phenyl propionate+2 MeOH         (1)

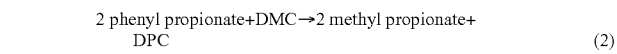

2 phenyl propionate+DMC→2 methyl propionate+DPC         (2)

2 PhOH+DMC→DPC+2 MeOH.         Net reaction

The disadvantage of such process involving the use of phenyl propionate as an intermediate is the necessity of having to recycle methyl propionate to the first step of the integrated process. This reduces overall efficiency. Further, and more importantly, since phenol is still used in said process the problem of an unfavorable reaction equilibrium is in fact just shifted to the first step wherein the phenol is reacted with methyl propionate. This implies that also in this first step large excesses of reagents are necessary, in this case to produce the intermediate phenyl propionate.

Another intermediate proposed in prior art (see e.g. U.S. Pat. No. 4,533,504) is one which is formed by reaction of phenol with ketene in a first step, which results in phenyl acetate. In a second step, this intermediate phenyl acetate is reacted with DMC into methyl acetate and the desired DPC. Finally, in a third step, said methyl acetate is converted into ketene and methanol. The ketene formed in the third step is recycled to the first step. The reactions in said three steps and the net reaction of the integrated process wherein ketene is recycled are shown below:

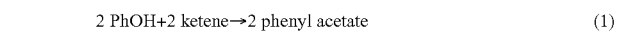

2 PhOH+2 ketene→2 phenyl acetate         (1)

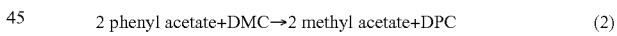

2 phenyl acetate+DMC→2 methyl acetate+DPC         (2)

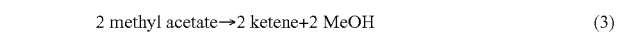

2 methyl acetate→2 ketene+2 MeOH         (3)

2 PhOH+DMC→DPC+2 MeOH.         Net reaction

Said process involving the recycle of ketene suffers from the same disadvantages as discussed above in respect of the process wherein methyl propionate is recycled to the first step. In addition, the former process suffers from the disadvantage that the first intermediate compound first has to be converted into a second intermediate compound which can then be converted into the ketene to be recycled.

Another process proposed in prior art (see e.g. U.S. Pat. No. 5,349,102) wherein phenyl acetate is used as an intermediate and which suffers from the same disadvantages as the above process wherein ketene is used, is one wherein in a first step said phenyl acetate and acetic acid are formed from phenol and acetic anhydride. Just like in the above process, in a second step phenyl acetate and DMC are converted into methyl acetate and DPC. However, in the third step, said methyl acetate is reacted with carbon monoxide resulting in acetic anhydride which is then recycled to the first step. The reactions in said three steps and the net reaction of the integrated process wherein acetic anhydride is recycled are shown below:

2 PhOH+2 acetic anhydride→2 phenyl acetate+2 acetic acid (1)

2 phenyl acetate+DMC→2 methyl acetate+DPC (2)

2 methyl acetate+2 CO→2 acetic anhydride (3)

2 PhOH+DMC+2 CO→DPC+2 acetic acid. Net reaction

In general, all of the above-mentioned integrated processes are disadvantageous in that several intermediates must be recyled in large amounts. In addition, certain by-products produced have such boiling point which makes it hard to separate the final product or valuable intermediate products.

For example, in a case where diphenyl carbonate (and methanol) is produced from dimethyl carbonate and phenol, always some anisole (methoxybenzene) is formed as a by-product. Anisole can be formed by reaction of the phenol with methanol and/or the dimethyl carbonate itself. Anisole has a boiling point which is close to the boiling point of the mixed carbonate methyl phenyl carbonate, which is formed as an intermediate. In a case where not all of the intermediate mixed carbonate has been converted into final diphenyl carbonate, it is highly desired to recover said mixed carbonate and to have it further reacted into final diphenyl carbonate. However, such recovery requires separation of the mixed carbonate from the anisole, e.g. by distillation, which is cumbersome because of a small difference in boiling points.

A further disadvantage associated with the use of an aromatic alcohol, such as phenol, in the preparation of diaryl carbonates, such as diphenyl carbonate, is that in a fully integrated process where said phenol has to be produced on the site itself, coproducts are made in addition to the desired phenol which may be undesired. The industrially most important process for preparing phenol is one wherein cumene (made by alkylation of benzene) is oxidised into cumene hydroperoxide which is then converted into phenol and acetone. If the acetone cannot be used on the site itself in any other process, it has to be sold.

In view of the above disadvantages associated with the use of an aromatic alcohol, such as phenol, in the preparation of diaryl carbonates, such as diphenyl carbonate, it would be highly desirable to be able to provide a process for the preparation of a diaryl carbonate which would not use an aromatic alcohol as a starting compound, not in the specific process step which results in the production of the desired diaryl carbonate and neither in any preceding process step.

SUMMARY OF THE INVENTION

The present inventor has provided such a process for the preparation of a diaryl carbonate, wherein no aromatic alcohol is used as a starting compound. The present invention relates to a process for the preparation of a diaryl carbonate, which comprises:

(i) contacting an aromatic non-hydroxy compound with a carboxylic acid of formula $$HOC(=O)R^1$$ (I), wherein $R^1$ is a hydrocarbyl group, and with an oxygen containing gas in the presence of a catalyst, resulting in water and an aromatic carboxylic acid ester of formula $$R^2OC(=O)R^1$$ (II), wherein $R^2$ is an aryl group originating from the aromatic non-hydroxy compound; and (ii) contacting the aromatic carboxylic acid ester of formula (II) from step (i) with a dialkyl carbonate of formula $$R^3OC(=O)OR^4$$ (III), wherein $R^3$ and $R^4$ are the same or different and are alkyl groups, in the presence of a catalyst, resulting in a diaryl carbonate of formula $$R^2OC(=O)OR^2$$ (IV)

and an alkyl carboxylic acid ester of formula $$R^5OC(=O)R^1$$ (V), wherein $R^5$ is $R^3$ or $R^4$.

DETAILED DESCRIPTION OF THE INVENTION

In one embodiment, where in the process of the present invention, in step (i) the aromatic non-hydroxy compound is benzene and the carboxylic acid of formula (I) is acetic acid, resulting in water and phenyl acetate as the aromatic carboxylic acid ester of formula (II), and in step (ii) the dialkyl carbonate of formula (III) is dimethyl carbonate (DMC), resulting in diphenyl carbonate (DPC) as the diaryl carbonate of formula (IV) and methyl acetate as the alkyl carboxylic acid ester of formula (V), the reactions in said two steps (i) and (ii) and the net reaction of the process are shown below:

2 benzene+2 acetic acid+O₂→2 phenyl acetate+2 H₂O (i)

2 phenyl acetate+DMC→2 methyl acetate+DPC (ii)

2 benzene+2 acetic acid+O₂+DMC→2 methyl acetate+DPC+2 H₂O. Net reaction

The advantage of such process is that no aromatic alcohol (e.g. phenol) is needed, that only one intermediate (e.g. phenyl acetate) is formed and that, in addition to the desired diaryl carbonate (e.g. DPC), a valuable co-product (e.g. methyl acetate) is formed that does not have to be recycled. The key benefit of the present process is that in the value chain from benzene to e.g. DPC, no phenol is required as a starting material in any step. Because of that, no excesses of the starting materials need to be used. Further, no complicated catalytic distillation techniques for driving a reaction into the thermodynamically disfavoured but desired direction, need to be applied, such as is the case when using phenol as a starting material.

As discussed above, step (ii) of the present process as such is known in prior art (see e.g. U.S. Pat. No. 5,543,546, U.S. Pat. No. 4,533,504, and U.S. Pat. No. 5,349,102). That is to say, it is known as such to contact an aromatic carboxylic acid ester of formula (II) (e.g. phenyl propionate or phenyl acetate) with a dialkyl carbonate of formula (III) (e.g. DMC), resulting in a diaryl carbonate of formula (IV) (e.g. DPC) and an alkyl carboxylic acid ester of formula (V) (e.g. methyl propionate or methyl acetate). However, in every prior art process comprising said reaction, the aromatic carboxylic acid ester is prepared in a preceding step using an aromatic alcohol as one of the starting materials.

Further, step (i) of the present process as such is known in prior art. That is to say, it is known as such to contact an aromatic non-hydroxy compound (e.g. benzene) with a carboxylic acid of formula (I) (e.g. acetic acid) and with an oxygen containing gas, resulting in water and an aromatic carboxylic acid ester of formula (II) (e.g. phenyl acetate). See e.g. U.S. Pat. No. 6,342,620. However, in every instance, the aromatic carboxylic acid ester prepared in such way is not subsequently used in a next step, similar to step (ii) of the present process, to produce a diaryl carbonate. On the contrary, said prior art teaches to hydrolyse the aromatic carboxylic acid ester in order to make an aromatic alcohol (e.g. phenol) and the carboxylic acid of formula (I), of which the latter is recycled to the first step. For said specificly exemplified case, the reactions in the two steps and the net reaction of the integrated process wherein acetic acid is recycled are shown below:

benzene+acetic acid+½O$_2$→phenyl acetate+H$_2$O  (1)

phenyl acetate+H$_2$O→phenol+acetic acid  (2)

benzene+½O$_2$→phenol.  Net reaction

In summary, such prior art processes wherein phenyl acetate is formed from benzene, acetic acid and oxygen, are only aimed at and connected with the production of phenol as a final product, not a diaryl carbonate, from said phenyl acetate.

As mentioned above, U.S. Pat. No. 6,342,620 discloses step (i) of the present process. In said step (i), an aromatic non-hydroxy compound is contacted with a carboxylic acid of formula

HOC(=O)R$^1$  (I), wherein R$^1$ is a hydrocarbyl group, and with an oxygen containing gas in the presence of a catalyst, resulting in water and an aromatic carboxylic acid ester of formula

R$^2$OC(=O)R$^1$  (II), wherein R$^2$ is an aryl group originating from the aromatic non-hydroxy compound.

The teaching of said U.S. Pat. No. 6,342,620 is incorporated herein by reference. The catalysts, reaction temperature, pressure, methodology disclosed in said U.S. Pat. No. 6,342,620 may also be practised in step (i) of the present process. The present process is, however, not restricted thereto.

Within the present specification, the term "aromatic non-hydroxy compound" means an aromatic compound which does not contain any hydroxyl groups. In other words, the aromatic compound which is used as a starting material in step (i) of the present process does not contain any hydroxyl groups. The aromatic non-hydroxy compound may be benzene. Further, it may be benzene containing (non-hydroxyl) substituents, such as biphenyl. Further, the aromatic non-hydroxy compound may be an aromatic compound consisting of two or more fused benzene rings, such as naphthalene and anthracene. Preferably, the aromatic non-hydroxy compound is (unsubstituted) benzene, in which case the aromatic carboxylic acid ester of formula (II) is a phenyl carboxylic acid ester of formula (II) wherein R$^2$ is a phenyl group and the diaryl carbonate of formula (IV) is diphenyl carbonate.

In step (i) of the present process, a carboxylic acid of formula HOC(=O)R$^1$ (I) is used. R$^1$ in the carboxylic acid of formula (I) may be a C$_1$-C$_{10}$ alkyl group, preferably a C$_1$-C$_5$ alkyl group, or it may be an aryl group. Said aryl group may be a phenyl group, which corresponds with the carboxylic acid of formula (I) being benzoic acid. Preferably, said R$^1$ is a methyl, ethyl or propyl group, which corresponds with the carboxylic acid of formula (I) preferably being acetic acid, propionic acid or butyric acid. Most preferably, the carboxylic acid of formula (I) is acetic acid, in which case the aromatic carboxylic acid ester of formula (II) is an aromatic acetate of formula (II) wherein R$^1$ is a methyl group.

According to a preferred embodiment of step (i) of the present process, the aromatic non-hydroxy compound is benzene and the carboxylic acid of formula (I) is acetic acid, in which case the aromatic carboxylic acid ester of formula (II) is phenyl acetate and the diaryl carbonate of formula (IV) is diphenyl carbonate.

As the catalyst in step (i), a catalyst containing a Group VIII metal (e.g. palladium), Group VIb metal (e.g. chromium) or Group Va metal (e.g. antimony) as the main catalyst ingredient, may be used.

The metal in said catalyst may be supported on a carrier which is inactive itself to the reaction in step (i). Said carrier may be an alumina, for example gamma alumina, active carbon or silica.

In consideration of the catalytic activity and cost, the amount of catalytically active metal (e.g. palladium) is usually in the range of 0.01 to 10 wt. %, preferably 0.1 to 5 wt. %, based on the weight of the support.

For example, any one of the palladium catalysts as taught in U.S. Pat. No. 6,342,620 may be used in step (i) of the present process. Where a palladium catalyst is used, the palladium raw material (or main catalyst ingredient) includes palladium metal and palladium compounds such as, for example, ammonium hexachloropalladate, potassium hexachloropalladate, sodium hexachloropalladate, ammonium tetrachloropalladate, potassium tetrachloropalladate, sodium tetrachloropalladate, potassium tetrabromopalladate, palladium oxide, palladium chloride, palladium bromide, palladium iodide, palladium nitrate, palladium sulfate, palladium acetate, potassium dinitrosulfite-palladate, chlorocarbonyl palladium, dinitrodiamminepalladium, tetraamminepalladium chloride, tetraamminepalladium nitrate, cis-diamminedichloropalladium, trans-diamminedichloro-palladium, dichloro(ethylenediamine)palladium, potassium tetracyanopalladate and acetylacetonatopalladium.

In addition to said main catalyst ingredient, a co-catalyst may be used in step (i) of the present process. The co-catalyst used includes, for example, metals such as gold, silver, copper, iron, manganese, cadmium, zinc, uranium, tin, thallium, lead, bismuth, antimony and tellurium, and compounds thereof. The metal compounds include, for example, oxides, hydroxides, nitrates, sulfates, carbonates, halides, oxyhalides, sulfides, organic carboxylates such as acetates, oxalates, naphthenates and stearates, and organic compounds. The amount of the co-catalyst is not particularly limited provided that a catalyst activity-enhancing effect is obtained.

In respect of methods for preparing any of the above-mentioned catalysts which contain palladium, explicit reference is made to U.S. Pat. No. 6,342,620.

The reaction temperature in step (i) is usually in the range of 100 to 300° C., preferably 150 to 250° C. The reaction pressure is usually in the range of 0.1 to 100 atmospheric pressure, preferably 0.5 to 50. Most preferably, the reaction in step (i) is carried out at atmospheric pressure.

The oxygen containing gas used in step (i) as an oxidizing agent may be pure oxygen or may contain, in addition to the oxygen, an inert gas such as nitrogen, helium or argon. Air may also be used as the oxygen containing gas. The optimum amount of oxygen varies depending upon the reaction temperature, the amount of catalyst and other factors, and is not particularly limited provided that the oxygen containing gas flowing through the reactor is out of the explosive range.

Preferably, the reaction in step (i) is continuously carried out in a fixed bed reactor. Further, said reaction may be carried out in the gaseous phase, which implies that all the reactants are in the gaseous phase, including the aromatic non-hydroxy compound and the carboxylic acid of formula (I). This is preferred. However, the reaction may also be carried out by bubbling the oxygen containing gas through a liquid mixture of said aromatic non-hydroxy compound and carboxylic acid.

In respect of any other operating parameters for step (i) of the present process, explicit reference is made to U.S. Pat. No. 6,342,620. The present invention resides in the advantageous combination of steps (i) and (ii) and not in each of steps (i) and (ii) as such.

As mentioned above, U.S. Pat. No. 5,543,546 discloses step (ii) of the present process, wherein a transesterification is performed. In said step (ii), the aromatic carboxylic acid ester of formula (II) from step (i) is contacted with a dialkyl carbonate of formula $$R^3OC(=O)OR^4 \qquad (III),$$

wherein $R^3$ and $R^4$ are the same or different and are alkyl groups, in the presence of a catalyst.

The teaching of said U.S. Pat. No. 5,543,546 is incorporated herein by reference. The catalysts, reaction temperature, pressure, methodology disclosed in said U.S. Pat. No. 5,543,546 may also be practised in step (ii) of the present process. The present process is, however, not restricted thereto.

In step (ii) of the present process, the dialkyl carbonate to be used has formula (III), wherein $R^3$ and $R^4$ are the same or different and are alkyl groups. Preferably, $R^3$ and $R^4$ in the dialkyl carbonate of formula (III) are the same and are a $C_1$-$C_{10}$ alkyl group, more preferably a $C_1$-$C_4$ alkyl group, and most preferably a methyl, ethyl, n-propyl or isopropyl group, which corresponds with said dialkyl carbonate most preferably being a dimethyl carbonate, diethyl carbonate, di(n-propyl) carbonate or di(isopropyl) carbonate.

Most preferably, the dialkyl carbonate of formula (III) is diethyl carbonate, in which case the alkyl carboxylic acid ester of formula (V) is an ethyl carboxylic acid ester of formula (V) wherein $R^5$ is an ethyl group.

According to a preferred embodiment of the present process, the aromatic non-hydroxy compound is benzene, the carboxylic acid of formula (I) is acetic acid, and the dialkyl carbonate of formula (III) is diethyl carbonate, in which case the aromatic carboxylic acid ester of formula (II) is phenyl acetate, the diaryl carbonate of formula (IV) is diphenyl carbonate, and the alkyl carboxylic acid ester of formula (V) is ethyl acetate.

Examples of transesterification catalysts which can be used in step (ii) of the present process, are: mineral acids such as sulfuric acid; sulfonic acids such as para-toluenesulfonic acid; solid acids such as ion exchange resins and zeolite; base such as sodium hydroxide; metal alkoxide such as tetraisopropoxide titanate, zirconium(IV) isopropoxide; Lewis acid such as aluminum chloride and titanium tetrachloride, and compounds producing Lewis acid; metal phenoxides such as lead phenoxide and phenoxytitanium; lead oxides; lead salts such as carbonates; metal acetylacetonate complex such as zirconium(IV) acetylacetonate, bis(acetylacetonato) copper (II), zinc(II) acetylacetonate and lithium acetylacetonate; organotin compounds such as dibutyltin oxide; titanium silicate; and metal-substituted aluminum phosphate.

Preferably, a homogeneous titanium based catalyst, e.g. Ti(OPh)$_4$, is used. When using a homogeneous catalyst, this is preferably first dissolved in a solvent and added as a catalyst solution to the reactor. As the solvent, the diaryl carbonate of formula (IV), e.g. diethyl carbonate, may be used.

When using a homogeneous catalyst and a distillation column as a reactor (reactive distillation), the catalyst solution may be supplied to a stage of the distillation column to which the aromatic carboxylic acid ester of formula (II) and/or the dialkyl carbonate of formula (III) are supplied, or to a different stage. In general, it is desirable to supply the catalyst to higher stages of the distillation column, e.g. the upper half of said column.

The minimum catalyst concentration in step (ii) of the present process is 0.1 ppm, preferably 1 ppm, and more preferably 10 ppm, based on the total amount of the aromatic carboxylic acid ester of formula (II) and the dialkyl carbonate of formula (III) as raw materials. The maximum catalyst concentration up to which the catalyst dissolves in a saturated state in the reaction liquid in the reactor is about 10 weight percent, preferably 5 weight percent, and more preferably 1 weight percent.

The method for supplying the raw materials to the reactor in step (ii) of the present process is not particularly limited. Where a reactive distillation column is used, the aromatic carboxylic acid ester of formula (II) is preferably fed to the upper half of the column and the dialkyl carbonate of formula (III) is preferably fed to the lower half of the column, e.g. where said ester and carbonate are phenyl acetate and diethyl carbonate, respectively. In the latter case, the diaryl carbonate of formula (IV) (e.g. diphenyl carbonate) may be obtained from the bottom of the distillation column, and the alkyl carboxylic acid ester of formula (V) (e.g. ethyl acetate) may be obtained from the top of the distillation column.

The reaction temperature in step (ii) of the present process may be of from 50 to 350° C., preferably 100 to 250° C., more preferably 150 to 200° C. The operating pressure in said step (ii) is a reduced pressure, normal pressure or increased. Preferably, the pressure is subatmospheric.

The reaction in step (ii) of the present process proceeds via formation of a mixed carbonate of formula $$R^5OC(=O)OR^2 \qquad (VII),$$

wherein $R^5$ is $R^3$ or $R^4$, which are as defined above. For example, in a case where the aromatic carboxylic acid ester of formula $R^2OC(=O)R^1$ (II) is phenyl acetate and the dialkyl carbonate of formula $R^3OC(=O)OR^4$ (III) is dimethyl carbonate, $R^5$ and $R^2$ in said mixed carbonate of formula (VII) are methyl and phenyl, respectively, said mixed carbonate thus being methyl phenyl carbonate.

In a case where a product stream produced in step (ii) of the present process, contains mixed carbonate of formula (VII), in addition to the desired diaryl carbonate of formula (IV), said mixed carbonate may be separated. The separated mixed carbonate may then either be recycled back to step (ii) of the present process or be reacted with itself in order to produce additional diaryl carbonate.

In respect of any other operating parameters for step (ii) of the present process, explicit reference is made to U.S. Pat. No. 5,543,546. The present invention resides in the advantageous combination of steps (i) and (ii) and not in each of steps (i) and (ii) as such.

Even though the alkyl carboxylic acid ester of formula (V) (e.g. methyl acetate or ethyl acetate) produced in step (ii) of the present process, is a valuable co-product, in some instances, e.g. where the world demand for said ester is reduced, it may be preferred to hydrolyse said ester. Therefore, according to a preferred embodiment, the process of the present invention further comprises:

(iii) contacting the alkyl carboxylic acid ester of formula (V) from step (ii) with water, in the presence of a catalyst, resulting in the carboxylic acid of formula (I) and an alkanol of formula $$R^5OH \qquad (VI),$$

wherein $R^5$ is $R^3$ or $R^4$, which are as defined above.

Hydrolysis of the alkyl carboxylic acid ester of formula (V) by contacting it with water, can be done using an acidic or basic catalyst. These and other conditions for effecting hydrolysis of esters resulting in a carboxylic acid and an alkanol are commonly known. See for example U.S. Pat. No. 4,352,940, which describes a method for hydrolysis of methyl acetate, the teaching of which is incorporated herein by reference.

Preferably, the water from step (i) is sent to and used in step (iii) of said preferred embodiment of the present process. This advantageously results in integration of step (i) with step (iii). Further, integration of step (iii) with step (i) may also advantageously be achieved. That is to say, preferably, the carboxylic acid of formula (I) from step (iii) is sent to and used in step (i). Such integrations advantageously reduce the costs of making the diaryl carbonate.

For a case, where in said preferred embodiment of the process of the present invention, in step (i) the aromatic non-hydroxy compound is benzene and the carboxylic acid of formula (I) is acetic acid, resulting in water and phenyl acetate as the aromatic carboxylic acid ester of formula (II), and in step (ii) the dialkyl carbonate of formula (III) is dimethyl carbonate (DMC), resulting in diphenyl carbonate (DPC) as the diaryl carbonate of formula (IV) and methyl acetate as the alkyl carboxylic acid ester of formula (V), the reactions in the three steps (i), (ii) and (iii) and the net reaction of the integrated process wherein acetic acid is recycled are shown below:

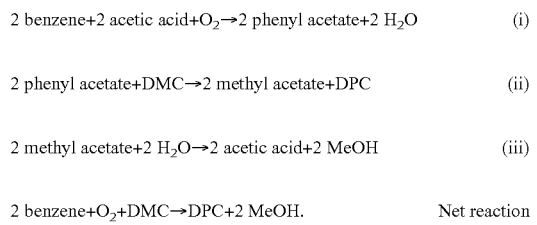

The alkanol of formula $R^5OH$ (VI) may also be recycled. More in particular, it is preferred that said alkanol of formula (VI) is sent to and used in a process for the preparation of the dialkyl carbonate of formula (III) from said alkanol and an alkylene carbonate (which is a cyclic carbonate). Said alkylene carbonate may be propylene carbonate or ethylene carbonate. For example, in a case where methanol is formed as the alkanol of formula (VI) in said step (iii) of the preferred embodiment of the present process, this may be sent to and used in a process wherein methanol and an alkylene carbonate are converted into dimethyl carbonate and monoalkylene glycol (or alkanediol). Such dialkyl carbonate of formula (III) may then favourably be used in step (ii) of the present process. With such additional recycle stream, even more integration is achieved, which further reduces the costs of making the desired diaryl carbonate of formula (IV).

Said alkylene carbonate may be prepared by reacting an alkylene oxide with carbon dioxide. Preferably, the alkylene oxide is propylene oxide or ethylene oxide.

Any process known for making dialkyl carbonate and alkylene glycol from alkylene carbonate and alkanol, may be applied. Further, any process known for making alkylene carbonate from alkylene oxide and carbon dioxide, may be applied.

To some extent, in the first step (i) of the present process also some carbon dioxide is formed. This may be caused by complete oxidation of the aromatic non-hydroxy compound and the aryl group $R^2$ from the aromatic carboxylic acid ester of formula (II). The specific concurrent side-reactions in a case where benzene is used and phenyl acetate is formed as the main product, are the following.

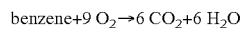

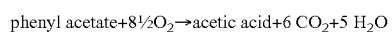

The carbon dioxide produced in this way may be separated and sent to and advantageously used in a process wherein an alkylene carbonate is prepared by reacting an alkylene oxide with carbon dioxide, rather than discharging the carbon dioxide into the environment, thereby in addition achieving even further integration of both processes. Thus, preferably, in such process the carbon dioxide comprises carbon dioxide which is formed as a by-product in step (i) of the present process.

The dialkyl carbonate of formula (III) to be used in step (ii) of the present process, may be prepared by reacting an alkylene carbonate with an alkanol as is described above. However, any other process for preparing said dialkyl carbonate may be applied as well.

The invention claimed is:

1. A process for preparing a diaryl carbonate, comprising:
    (i) contacting an aromatic non-hydroxy compound with a carboxylic acid of formula

wherein $R^1$ is a hydrocarbyl group, and with an oxygen containing gas in the presence of a catalyst, resulting in water and an aromatic carboxylic acid ester of formula

wherein $R^2$ is an aryl group originating from the aromatic non-hydroxy compound; and
    (ii) contacting the aromatic carboxylic acid ester of formula (II) from step (i) with a dialkyl carbonate of formula

wherein $R^3$ and $R^4$ are the same or different and are alkyl groups, in the presence of a catalyst, resulting in a diaryl carbonate of formula

and an alkyl carboxylic acid ester of formula

wherein $R^5$ is $R^3$ or $R^4$.

2. A process as claimed in claim 1, further comprising:
    (iii) contacting the alkyl carboxylic acid ester of formula (V) from step (ii) with water, in the presence of a catalyst, resulting in the carboxylic acid of formula (I) and an alkanol of formula

3. A process as claimed in claim 2, wherein the water from step (i) is sent to and used in step (iii).

4. A process as claimed in claim 2, wherein the carboxylic acid of formula (I) from step (iii) is sent to and used in step (i).

5. A process as claimed in claim 2, wherein the alkanol of formula (VI) is sent to and used in a process for the preparation of the dialkyl carbonate of formula (III) from said alkanol and an alkylene carbonate.

6. A process as claimed in claim 5, wherein the alkylene carbonate is propylene carbonate or ethylene carbonate.

7. A process as claimed in claim 5, wherein the alkylene carbonate is prepared by reacting an alkylene oxide with carbon dioxide.

8. A process as claimed in claim 7, wherein the alkylene oxide is propylene oxide or ethylene oxide.

9. A process as claimed in claim 7, wherein the carbon dioxide comprises carbon dioxide which is formed as a by-product in step (i).

10. A process as claimed in claim 1, wherein the aromatic non-hydroxy compound is benzene, the aromatic carboxylic acid ester of formula (II) is a phenyl carboxylic acid ester of formula (II) wherein $R^2$ is a phenyl group and the diaryl carbonate of formula (IV) is diphenyl carbonate.

11. A process as claimed in claim 1, wherein $R^1$ in the carboxylic acid of formula (I) is a $C_1$-$C_{10}$ alkyl group, preferably a methyl, ethyl or propyl group.

12. A process as claimed in claim 11, wherein the carboxylic acid of formula (I) is acetic acid and the aromatic carboxylic acid ester of formula (II) is an aromatic acetate of formula (II) wherein $R^1$ is a methyl group.

13. A process as claimed in claim 12, wherein the aromatic non-hydroxy compound is benzene, the aromatic carboxylic acid ester of formula (II) is phenyl acetate and the diaryl carbonate of formula (IV) is diphenyl carbonate.

14. A process as claimed in claim 1, wherein $R^3$ and $R^4$ in the dialkyl carbonate of formula (III) are the same and are a $C_1$-$C_{10}$ alkyl group, preferably a $C_1$-$C_4$ alkyl group, and more preferably a methyl, ethyl, n-propyl or isopropyl group.

15. A process as claimed in claim 14, wherein the dialkyl carbonate of formula (III) is diethyl carbonate and the alkyl carboxylic acid ester of formula (V) is an ethyl carboxylic acid ester of formula (V) wherein $R^5$ is an ethyl group.

16. A process as claimed in claim 15, wherein the aromatic non-hydroxy compound is benzene, the aromatic carboxylic acid ester of formula (II) is phenyl acetate, the diaryl carbonate of formula (IV) is diphenyl carbonate and the alkyl carboxylic acid ester of formula (V) is ethyl acetate.

* * * * *